(12) United States Patent
Umbarkar et al.

(10) Patent No.: US 10,106,487 B2
(45) Date of Patent: Oct. 23, 2018

(54) OXIDATIVE DEHYDROGENATION OF LACTATE ESTERS TO PYRUVATE ESTERS

(71) Applicant: Council of Scientific & Industrial Research, New Delhi (IN)

(72) Inventors: Shubhangi Bhalchandra Umbarkar, Pune (IN); Mohan Keraba Dongare, Pune (IN); Swati Laxmikantrao Pandhare, Pune (IN); Sonali Balasaheb Khomane, Pune (IN); Dhananjay Shahauraj Doke, Pune (IN)

(73) Assignee: COUNCIL OF SCIENTIFIC & INDUSTRIAL RESEARCH (IN)

( * ) Notice: Subject to any disclaimer, the term of this patent is extended or adjusted under 35 U.S.C. 154(b) by 0 days.

(21) Appl. No.: 15/735,530

(22) PCT Filed: Jun. 10, 2016

(86) PCT No.: PCT/IN2016/050181
§ 371 (c)(1),
(2) Date: Dec. 11, 2017

(87) PCT Pub. No.: WO2016/199174
PCT Pub. Date: Dec. 15, 2016

(65) Prior Publication Data
US 2018/0141892 A1    May 24, 2018

(30) Foreign Application Priority Data
Jun. 10, 2015   (IN) .......................... 1740/DEL/2015

(51) Int. Cl.
*C07C 67/313*   (2006.01)

(52) U.S. Cl.
CPC .................................. *C07C 67/313* (2013.01)

(58) Field of Classification Search
CPC ........................... C07C 67/313; C07C 67/317
See application file for complete search history.

(56) References Cited

U.S. PATENT DOCUMENTS 4,792,620 A * 12/1988 Paulik .................. B01J 31/0231
560/232

FOREIGN PATENT DOCUMENTS

JP         2011057660 A *   3/2011

OTHER PUBLICATIONS

Norskov et al, Nature Chemistry, Towards the Computational Design of Solid Catalysts, 2009, 1, pp. 37-46. (Year: 2009).*
Tanaka et al, Angewandte Chemie International Edition, a-Keto Esters and a-Keto Nitriles via Ruthenium Catalyzed Dehydrogenation of a-Hydroxy Esters and Cyanohydrins with tert-Butyl Hydroperoxide, 1984, 23(7), p. 518. (Year: 1984).*

* cited by examiner

*Primary Examiner* — Paul A Zucker
(74) *Attorney, Agent, or Firm* — Blank Rome LLP

(57) ABSTRACT

The present invention relates to a simple one step oxidative dehydrogenation process for the synthesis of alkyl pyruvate with 100% selectivity towards alkyl pyruvate comprising reacting an alkyl lactate in the presence of catalyst at the temperature ranging from 25-100° C. for the time period ranging from 5 to 40 hours in an organic solvent and hydrogen peroxide to afford alkyl pyruvate.

6 Claims, No Drawings

OXIDATIVE DEHYDROGENATION OF LACTATE ESTERS TO PYRUVATE ESTERS

This application is a national stage of International Patent Application No. PCT/IN2016/050181, filed Jun. 10, 2016, which claims the benefit of India Patent Application 1740/DEL/2015, filed Jun. 10, 2015, each of which is hereby incorporated by reference in its entirety.

FIELD OF THE INVENTION

The present invention relates to an oxidative dehydrogenation process for the synthesis of pyruvates from lactates. More particularly, the present invention relates to a process for the synthesis of pyruvates from lactates with 100% selectivity towards pyruvates.

BACKGROUND AND PRIOR ART OF THE INVENTION

Pyruvic acid and pyruvates (pyruvic acid esters) are important intermediates for perfumes, food additives, and electronic materials as well as raw materials for various bioactive substances such as antiviral drugs. It is used as flavours for food.

Conventionally pyruvic acid is produced by dehydrative decarboxylation of tartaric acid. Silica-supported pyrosulfate catalyst ($K_2S_2O_7/SiO_2$) is used for synthesis of ethyl pyruvate in continuous mode with up to 60% yields at the high temperature of 300° C. This reaction requires excess $KHSO_4$ as a dehydrating agent, leading to an expensive and wasteful process. Pyruvate can also be obtained by a microbial process, using strains of yeast and *E. coli*. However, both strains require precise regulation of media composition during fermentation and complex supplements.

Article titled "New technique on synthesis of ethyl pyruvate" by Chen Sufang et al. reports ethyl pyruvate was synthesized from ethyl lactate using TBHP as oxidant and TBAB as phase transfer catalyst, the purity of product was over 98%. The reaction is environment friendly and easy to operate, it provides a new method to synthesize ethyl pyruvate from ethyl lactate.

U.S. Pat. No. 5,053,527 discloses a process for the manufacture of alkyl pyruvates having the general formula: $CH_3$—CO—COOR; wherein R represents a $C_1$-$C_8$ alkyl radical, by oxidation of the corresponding alkyl lactate, the improvement comprising; admixing a 30 to 70% by weight aqueous hydrogen peroxide solution into a solution of the alkyl lactate in an organic water-immiscible solvent containing a catalytic quantity of bromine while maintaining a temperature of 15°–30° C.

Article titled "Titania-catalysed oxidative dehydrogenation of ethyl lactate: effective yet selective free-radical oxidation" by Enrique V. Ramos-Fernandez et al. published in *Green Chemistry*, 2014, 16, pp 3358 reports the catalytic oxidative dehydrogenation of ethyl lactate, as an alternative route to ethyl pyruvate. Testing various solid catalysts ($Fe_2O_3$, $TiO_2$, $V_2O_5/MgO$—$Al_2O_3$, $ZrO_2$, $CeO_2$ and ZnO). The liquid phase oxidation of ethyl lactate 1 was carried out in a 400 ml stirred autoclave (Biometa, fitted with a system for liquid sampling) at 403 K and at constant pressure of 1 MPa of pure oxygen. The catalyst (2 g) was immersed in 200 g of ethyl lactate. In experiments using a solvent, mass ratio of 1:1 (solvent:reactant) was used.

Article titled "Catalytic activity of iron phosphate doped with a small amount of molybdenum in the oxidative dehydrogenation of lactic acid to pyruvic acid" by Mamoru Ai published in *Applied Catalysis A General* 234(1):235-243 reports both the catalytic activity and the selectivity of iron phosphate in the oxidative dehydrogenation of lactic acid to form pyruvic acid increase dramatically by doping a very small amount of molybdenum compounds. Both the highest activity and selectivity are obtained at a Mo/Fe atomic ratio ranging from 0.01 to 0.3. The catalytic activity and selectivity are not affected if the source of $Mo^{6+}$ is changed. Effects similar to those for the $Mo^{6+}$ doping are not observed in the cases of the doping of $V^{5+}$ or $W^{6+}$. The functions of Mo6+ were studied.

Article titled "Efficient oxidative dehydrogenation of lactate to pyruvate using a gas-liquid micro flow system" by Toshiya Yasukawa et al. published in *Industrial and Engineering Chemistry Research*, 2011, 50 (7), pp 3858-3863 reports an efficient production of pyruvate by the oxidative dehydrogenation of lactate is achieved using a micro flow system based on gas-liquid slug flow. In this micro flow system, oxidizing agents and acetonitrile solutions of lactates and vanadium species are used, and lactate is converted into the corresponding pyruvate. For reasons of atom economy and enhanced mass transfer of oxygen into the liquid phase, due to internal circulation flow within slugs, molecular oxygen is the preferred agent. In a catalyst screening, vanadium oxytrichloride ($VOCl_3$) gave the highest pyruvate yield. A continuous system is developed, consisting of the following two processes using T-shaped mixers: the mixing of an acetonitrile solution of lactate with that of $VOCl_3$ and the injection of oxygen gas into the solution mixture. Compared with the conventional batch system, the oxidative dehydrogenation of lactate to the corresponding pyruvate proceeds more effectively using this micro flow system.

Chinese Pat. No. 1060759 discloses the catalytic oxidation synthesis of pyruvate is characterized by that in the presence of modified silver or copper catalyst said invention uses gas phase atmospheric oxidation of lactate to prepare pyruvate. Its dressing agent is a halide, and one or several kinds of P, Zr, Zn and K also can be added. Its reaction temp. is 300-600 deg. C., and according to different technological processes, the crude pyruvate products with low concentration and high concentration can be respectively prepared, and after rectification the invented refined product can be obtained. There are a variety of methods known in the art for preparing pyruvic acid esters, for example ethyl lactate, petroleum ether, sodium dihydrogen phosphate, potassium permanganate reacted together, with potassium permanganate as the oxidizing agent lactate, and acetone esters evaporated. Also some hydrogen peroxide as an oxidant lactate production and pyruvate. Such methods are adding an oxidizing agent in the lactate ester in the liquid phase oxidation of lactate to pyruvate, and then isolated and purified.

U.S. Pat. No. 4,229,590 reports alkyl pyruvates are prepared by oxidizing alkyl lactates in the presence of a silver catalyst of a defined particle size, at from 450° to 700° C. The products are starting materials for the preparation of drugs, synthetic resins and plastics.

US Pat. No. 887,795 reports a method for preparing a pyruvate ester is disclosed. In the method of the present invention, a lactate ester is oxidized by hydrogen peroxide in the presence of a Ti—Si molecular sieve catalyst. In the present invention, the Ti—Si molecular sieve catalyst is easily filtered and recycled, the reaction conditions are mild due to the usage of hydrogen peroxide, the process is simple and easily performed, the conversion rate of the lactate ester is high, and the selectivity of the pyruvate ester is high.

Chinese Pat. No. 104276951 discloses an aqueous-phase catalytic oxidation method for preparing lactate pyruvate, Pt load which bismuth compound or Pd as catalyst and molecular oxygen as oxidant, water as solvent, the selective and efficient preparation of pyruvate oxidation lactates, The process mild reaction conditions, high selectivity, the catalyst can be reused, has important application prospects.

Chinese Pat. No. 1359893 discloses a process for preparing ethyl pyruvate is characterized by that the reaction of the mixture of ethyl lactate vapour and air at 250-300 deg. C. in the presence of silica gel carried silver catalyst. Its advantages are high conversion (80%) and selectivity (90%), and high activity and selectivity of catalyst. Therefore, there is a need to develop a suitable catalyst for high yield synthesis of ethyl pyruvate from ethyl lactate.

SUMMARY OF THE INVENTION

The main objective of the present invention is to provide a simple one step oxidative dehydrogenation process for the synthesis of pyruvates from lactates with selectivity and yields for pyruvates.

Another objective of the present invention is to provide a simple process for the synthesis of pyruvates from lactates with 100% selectivity in presence of easily available catalysts and oxidizing agent.

Accordingly, the present invention provides a simple one step oxidative dehydrogenation process for the synthesis of alkyl pyruvate comprising reacting an alkyl lactate with peroxides in the presence of catalyst at the temperature ranging from 25-100 deg C. for the time period ranging from 5 to 40 hours in an organic solvent to afford alkyl pyruvate.

In an embodiment, said alkyl lactates are selected from the group consisting of methyl lactate, ethyl lactate, propyl lactate, butyl lactate and such like.

In another embodiment, said solvent is selected from the group consisting of water, acetonitrile, methanol, ethanol and toluene.

In still another embodiment, said catalyst is selected from salts of transition metals.

In a preferred embodiment, said metals are in the form of salts, oxides and hydroxides.

In another preferred embodiment, said metals are selected from the group consisting of Co, Cr, Fe, Mo, V, W, Ti, Cu, Cr, Ru, Mn, Ag, Au, Ni, Pd, or Pt.

In still another preferred embodiment, said peroxides are selected from the group consisting of tert-butyl hydrogen peroxide and meta chloroperbenzoic acid.

In yet another embodiment, said process of the invention for the synthesis of alkyl pyruvates results in >90% selectivity towards the pyruvates.

In a preferred embodiment, said process provides 100% selectivity towards the pyruvates.

In still yet another embodiment, said process provides up to 98% conversion of alkyl lactates.

DETAILED DESCRIPTION OF THE INVENTION

The invention will now be described in detail in connection with certain preferred and optional embodiments, so that various aspects thereof may be more fully understood and appreciated.

The present invention relates to a simple one step oxidative dehydrogenation process for the synthesis of alkyl pyruvate with 100% selectivity towards alkyl pyruvate comprising reacting an alkyl lactate in the presence of catalyst at the temperature ranging from 25-100° C. for the time period ranging from 5 to 40 hours in an organic solvent and peroxide to afford alkyl pyruvate.

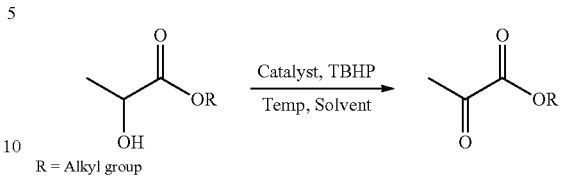

R = Alkyl group

In preferred embodiment, said alkyl lactates are selected from methyl lactate, ethyl lactate, propyl lactate, butyl lactate and such like.

In another preferred embodiment, said solvent is selected from water, acetonitrile, methanol, ethanol and toluene.

In still yet another preferred embodiment, said process is carried out with solvent or without solvent.

In still another preferred embodiment, said catalyst is selected from salts of transition metals.

In yet another preferred embodiment, said metals are in the form of salts, oxides and hydroxides.

In still yet another preferred embodiment, said metals are Co, Cr, Fe, Mo, V, W, Ti, Cu, Cr, Ru, Mn, Ag, Au, Ni, Pd, or Pt.

In still yet another preferred embodiment, said peroxides are selected from tert-butyl hydrogen peroxide, m-chloroperbenzoic acid.

In an embodiment, said process of the invention for the synthesis of alkyl pyruvates results in >90% selectivity towards the pyruvates.

In another embodiment, said process provides 100% selectivity towards the pyruvates.

In still another embodiment, said process provides up to 98% conversion of alkyl lactates.

The following examples, which include preferred embodiments, will serve to illustrate the practice of this invention, it being understood that the particulars shown are by way of example and for purpose of illustrative discussion of preferred embodiments of the invention.

EXAMPLES

Example 1

Oxidative dehydrogenation of ethyl lactate to ethyl pyruvate was carried out using $MoO_2Cl_2(DMSO)_2$; (DMSO=dimethyl sulfoxide) as catalyst. A 50 ml two necked round bottom flask was charged with 0.5 g ethyl lactate, 10 g acetonitrile, 1.5 mL tert-butyl hydrogenperoxide (5-6 M in decane) and 0.030 g $MoO_2Cl_2.2DMSO$ as catalyst. The solution was heated at 80° C. for 19 h. In this reaction 92% conversion of ethyl lactate was obtained with 100% selectivity for ethyl pyruvate.

Example 2

Oxidative dehydrogenation of ethyl lactate to ethyl pyruvate was carried out using $MoO_2Cl_2$ bipy; (bipy=bipyridine) as catalyst. A 50 ml two necked round bottom flask was charged with 0.5 g ethyl lactate, 10 g acetonitrile, 1.5 mL tert-butyl hydrogenperoxide (5-6 M in decane) and 0.0276 g $MoO_2Cl_2$ (bipy) as catalyst. The solution was heated at 80°

C. for 19 h. In this reaction 19% conversion of ethyl lactate was obtained with 100% selectivity for ethyl pyruvate Example 3

Oxidative dehydrogenation of ethyl lactate to ethyl pyruvate was carried out using $MoO_2Cl_2(DMF)_2$; (DMF=dimethyl formamide) as catalyst. A 50 ml two necked round bottom flask was charged with 0.5 g ethyl lactate, 10 g acetonitrile, 1.5 mL tert-butyl hydrogenperoxide (5-6 M in decane) and 0.0291 g $MoO_2Cl_2.(DMF)_2$ as catalyst. The solution was heated at 80° C. for 17 h. In this reaction 96% conversion of ethyl lactate was obtained with 100% selectivity for ethyl pyruvate.

Example 4

Oxidative dehydrogenation of ethyl lactate to ethyl pyruvate was carried out using $MoO_2Cl_2.(benzthiozole)_2$ as catalyst. A 50 ml two necked round bottom flask was charged with 0.5 g ethyl lactate, 10 g acetonitrile, 1.5 mL tert-butyl hydrogenperoxide (5-6 M in decane) and 0.0276 g $MoO_2Cl_2.2benzthiozole$ as catalyst. The solution was heated at 80° C. for 15 h. In this reaction 70% conversion of ethyl lactate was obtained with 100% selectivity for ethyl pyruvate.

Example 5

Oxidative dehydrogenation of ethyl lactate to ethyl pyruvate was carried out using $MoO_3$ as catalyst. A 50 ml two necked round bottom flask was charged with 0.5 g ethyl lactate, 10 g acetonitrile, 1.5 mL tert-butyl hydrogenperoxide (5-6 M in decane) and 0.0276 g $MoO_3$ as catalyst. The solution was heated at 80° C. for 17 h. In this reaction 36% conversion of ethyl lactate was obtained with 100% selectivity for ethyl pyruvate.

Example 6

Oxidative dehydrogenation of ethyl lactate to ethyl pyruvate was carried out using $VO(acac)_2$ as catalyst. A 50 ml two necked round bottom flask was charged with 0.5 g ethyl lactate, 10 g acetonitrile, 1.5 mL tert-butyl hydrogenperoxide (5-6 M in decane) and 0.0215 g $VO(acac)_2$ as catalyst. The solution was heated at 80° C. for 15 h. In this reaction 80% conversion of ethyl lactate was obtained with 100% selectivity for ethyl pyruvate.

Example 7

Oxidative dehydrogenation of ethyl lactate to ethyl pyruvate was carried out using copper acetate as catalyst. A 50 ml two necked round bottom flask was charged with 0.5 g ethyl lactate, 10 g acetonitrile, 1.5 mL tert-butyl hydrogenperoxide (5-6 M in decane) and 0.0091 g Copper acetate as catalyst. The solution was heated at 80° C. for 11 h. In this reaction 46% conversion of ethyl lactate was obtained with 100% selectivity for ethyl pyruvate.

Example 8

Oxidative dehydrogenation of methyl lactate to methyl pyruvate was carried out using $MoO_2Cl_2(DMF)_2$; (DMF=dimethyl formamide) as catalyst. A 50 ml two necked round bottom flask was charged with 0.5 g methyl lactate, 10 g acetonitrile, 1.5 mL tert-butyl hydrogenperoxide (5-6 M in decane) and 0.0330 g $MoO_2Cl_2(DMF)_2$ as catalyst. The solution was heated at 80° C. for 14 h. In this reaction 43% conversion of methyl lactate was obtained with 100% selectivity for methyl pyruvate.

Example 9

Oxidative dehydrogenation of ethyl lactate to ethyl pyruvate was carried out using $MoO_2Cl_2(DMF)_2$; (DMF=dimethyl formamide) as catalyst. A 50 ml two necked round bottom flask was charged with 0.5 g ethyl lactate, no solvent, 1.5 mL tert-butyl hydrogenperoxide (5-6 M in decane) and 0.0291 g $MoO_2Cl_2.(DMF)_2$ as catalyst. The solution was kept at room temperature for 36 h. In this reaction 3% conversion of ethyl lactate was obtained with 100% selectivity for ethyl pyruvate.

Example 10

Oxidative dehydrogenation of ethyl lactate to ethyl pyruvate was carried out using $MoO_2Cl_2(DMF)_2$; (DMF=dimethyl formamide) as catalyst. A 50 ml two necked round bottom flask was charged with 0.5 g ethyl lactate, 10 g acetonitrile, 1.5 mL tert-butyl hydrogenperoxide (5-6 M in decane) and 0.0291 g $MoO_2Cl_2.(DMF)_2$ as catalyst. The solution was heated at 50° C. for 11 h. In this reaction 6% conversion of ethyl lactate was obtained with 100% selectivity for ethyl pyruvate.

Example 11

Oxidative dehydrogenation of ethyl lactate to ethyl pyruvate was carried out using cobalt (II) chloride as catalyst. A 50 ml two necked round bottom flask was charged with 0.5 g ethyl lactate, 10 g acetonitrile, 1.5 mL tert-butyl hydrogenperoxide (5-6 M in decane) and 0.0199 g cobalt (II) chloride as catalyst. The solution was heated at 80° C. for 11 h. In this reaction 82% conversion of ethyl lactate was obtained with 100% selectivity for ethyl pyruvate.

Example 12

Oxidative dehydrogenation of ethyl lactate to ethyl pyruvate was carried out using $MoO_2Cl_2(DMF)_2$; (DMF=dimethyl formamide) as catalyst. A 50 ml two necked round bottom flask was charged with 0.5 g ethyl lactate, 10 g acetonitrile, 1.5 mL tert-butyl hydrogenperoxide (5-6 M in decane) and 0.0144 g $MoO_2Cl_2.(DMF)_2$ (1 mol %) as catalyst. The solution was heated at 80° C. for 11 h. In this reaction 56% conversion of ethyl lactate was obtained with 100% selectivity for ethyl pyruvate.

Example 13

Oxidative dehydrogenation of ethyl lactate to ethyl pyruvate was carried out using $MoO_2Cl_2(DMF)_2$; (DMF=dimethyl formamide) as catalyst. A 50 ml two necked round bottom flask was charged with 0.5 g ethyl lactate, 10 g acetonitrile, 1.5 mL tert-butyl hydrogenperoxide (5-6 M in decane) and 0.0072 g $MoO_2Cl_2.(DMF)_2$ (0.5 mol %) as catalyst. The solution was heated at 80° C. for 11 h. In this reaction 11% conversion of ethyl lactate was obtained with 100% selectivity for ethyl pyruvate.

Example 14

Oxidative dehydrogenation of ethyl lactate to ethyl pyruvate was carried out using $MoO_2Cl_2(DMF)_2$;

(DMF=dimethyl formamide) as catalyst. A 50 ml two necked round bottom flask was charged with 0.5 g ethyl lactate, 10 g acetonitrile, 1.5 mL tert-butyl hydrogenperoxide (5-6 M in decane) and 0.0722 g $MoO_2Cl_2.(DMF)_2$ (5 mol %) as catalyst. The solution was heated at 80° C. for 11 h. In this reaction 72% conversion of ethyl lactate was obtained with 100% selectivity for ethyl pyruvate.

Example 15

Oxidative dehydrogenation of ethyl lactate to ethyl pyruvate was carried out using $MoO_2Cl_2(DMF)_2$; (DMF=dimethyl formamide) as catalyst. A 50 ml two necked round bottom flask was charged with 0.5 g ethyl lactate, 10 g acetonitrile, 1.5 mL tert-butyl hydrogenperoxide (5-6 M in decane) and 0.0291 g $MoO_2Cl_2.(DMF)_2$ as catalyst. The solution was kept at room temperature for 38 h. In this reaction 6% conversion of ethyl lactate was obtained with 100% selectivity for ethyl pyruvate.

Example 16

Oxidative dehydrogenation of ethyl lactate to ethyl pyruvate was carried out using as iron (III) chloride catalyst. A 50 ml two necked round bottom flask was charged with 0.5 g ethyl lactate, 10 g acetonitrile, 1.5 mL tert-butyl hydrogenperoxide (5-6 M in decane) and 0.0137 g iron (III) chloride as catalyst. The solution was heated at 80° C. for 9 h. In this reaction 63% conversion of ethyl lactate was obtained with 100% selectivity for ethyl pyruvate.

Example 17

Oxidative dehydrogenation of ethyl lactate to ethyl pyruvate was carried out using $MoO_2Cl_2(DMF)_2$; (DMF=dimethyl formamide) as catalyst. A 50 ml two necked round bottom flask was charged with 0.5 g ethyl lactate, no solvent, 1.5 mL tert-butyl hydrogenperoxide (5-6 M in decane) and 0.0291 g $MoO_2Cl_2.(DMF)_2$ as catalyst. The solution was heated at 80° C. for 10 h. In this reaction 27% conversion of ethyl lactate was obtained with 100% selectivity for ethyl pyruvate.

Example 18

Oxidative dehydrogenation of ethyl lactate to ethyl pyruvate was carried out using Silver nitrate as catalyst. A 50 ml two necked round bottom flask was charged with 0.5 g ethyl lactate, 10 g acetonitrile, 1.5 mL tert-butyl hydrogenperoxide (5-6 M in decane) and 0.0143 g silver nitrate as catalyst. The solution was heated at 80° C. for 10 h. In this reaction 62% conversion of ethyl lactate was obtained with 100% selectivity for ethyl pyruvate.

Example 19

Oxidative dehydrogenation of ethyl lactate to ethyl pyruvate was carried out using palladium (II) acetate as catalyst. A 50 ml two necked round bottom flask was charged with 0.5 g ethyl lactate, 10 g acetonitrile, 1.5 mL tert-butyl hydrogenperoxide (5-6 M in decane) and 0.0189 g palladium (II) acetate as catalyst. The solution was heated at 80° C. for 11 h. In this reaction 36% conversion of ethyl lactate was obtained with 100% selectivity for ethyl pyruvate.

Example 20

Oxidative dehydrogenation of ethyl lactate to ethyl pyruvate was carried out using platinum (II) acetylacetone as catalyst. A 50 ml two necked round bottom flask was charged with 0.5 g ethyl lactate, 10 g acetonitrile, 1.5 mL tert-butyl hydrogenperoxide (5-6 M in decane) and 0.0332 g platinum (II) acetylacetone as catalyst. The solution was heated at 80° C. for 9 h. In this reaction 56% conversion of ethyl lactate was obtained with 100% selectivity for ethyl pyruvate.

Example 21

Oxidative dehydrogenation of ethyl lactate to ethyl pyruvate was carried out using gold chloride as catalyst. A 50 ml two necked round bottom flask was charged with 0.5 g ethyl lactate, 10 g acetonitrile, 1.5 mL tert-butyl hydrogenperoxide (5-6 M in decane) and 0.0256 g gold chloride as catalyst. The solution was heated at 80° C. for 24 h. In this reaction 94% conversion of ethyl lactate was obtained with 100% selectivity for ethyl pyruvate.

Example 22

Oxidative dehydrogenation of ethyl lactate to ethyl pyruvate was carried out using nickel chloride as catalyst. A 50 ml two necked round bottom flask was charged with 0.5 g ethyl lactate, 10 g acetonitrile, 1.5 mL tert-butyl hydrogenperoxide (5-6 M in decane) and 0.0109 g nickel chloride as catalyst. The solution was heated at 80° C. for 24 h. In this reaction 96% conversion of ethyl lactate was obtained with 100% selectivity for ethyl pyruvate.

Example 23

Oxidative dehydrogenation of ethyl lactate to ethyl pyruvate was carried out using ruthenium acetylacetonate as catalyst. A 50 ml two necked round bottom flask was charged with 0.5 g ethyl lactate, 10 g acetonitrile, 1.5 mL tert-butyl hydrogenperoxide (5-6 M in decane) and 0.0337 g ruthenium acetylacetonate as catalyst. The solution was heated at 80° C. for 10 h. In this reaction 50% conversion of ethyl lactate was obtained with 100% selectivity for ethyl pyruvate.

Example 24

Oxidative dehydrogenation of ethyl lactate to ethyl pyruvate was carried out using potassium dichromate as catalyst. A 50 ml two necked round bottom flask was charged with 0.5 g ethyl lactate, 10 g acetonitrile, 1.5 mL tert-butyl hydrogenperoxide (5-6 M in decane) and 0.0248 g potassium dichromate as catalyst. The solution was heated at 80° C. for 10 h. In this reaction 68% conversion of ethyl lactate was obtained with 100% selectivity for ethyl pyruvate.

Example 25

Oxidative dehydrogenation of ethyl lactate to ethyl pyruvate was carried out using sodium tungstate as catalyst. A 50 ml two necked round bottom flask was charged with 0.5 g ethyl lactate, 10 g acetonitrile, 1.5 mL tert-butyl hydrogenperoxide (5-6 M in decane) and 0.0279 g sodium tungstate as catalyst. The solution was heated at 80° C. for 10 h. In this reaction 12% conversion of ethyl lactate was obtained with 100% selectivity for ethyl pyruvate.

Example 26

Oxidative dehydrogenation of ethyl lactate to ethyl pyruvate was carried out using potassium titanium oxalate as catalyst. A 50 ml two necked round bottom flask was charged with 0.5 g ethyl lactate, 10 g acetonitrile, 1.5 mL tert-butyl hydrogenperoxide (5-6 M in decane) and 0.0299 g potassium titanium oxalate as catalyst. The solution was heated at 80° C. for 10 h. In this reaction 10% conversion of ethyl lactate was obtained with 100% selectivity for ethyl pyruvate.

Example 27

Oxidative dehydrogenation of ethyl lactate to ethyl pyruvate was carried out using VO(acac)$_2$ as catalyst. A 50 ml two necked round bottom flask was charged with 0.5 g ethyl lactate, 10 g acetonitrile, 1.4 g meta chloroperbenzoic acid (MCPBA) and 0.0215 g VO(acac)$_2$ as catalyst. The solution was heated at 80° C. for 24 h. In this reaction 50% conversion of ethyl lactate was obtained with 100% selectivity for ethyl pyruvate.

Following table 1 shows catalytic activity data for lactate to pyruvate.

TABLE 1

Catalytic activity data for lactate to pyruvate

| Example No. | Substrate | Catalyst, loading | Oxidant | Solvent | Temp °C. | Time h | Conversion % | Sel. % |
|---|---|---|---|---|---|---|---|---|
| 1 | Et lactate (0.5 g) | MoO$_2$Cl$_2$(DMSO)$_2$, 0.03 g | TBHP (org) 1.5 ml | CH$_3$CN 10 g | 80 | 19 | 92 | 100 |
| 2 | Et lactate (0.5 g) | MoO$_2$Cl$_2$bipy 0.0276 g | TBHP (org) 1.5 ml | CH$_3$CN 10 g | 80 | 19 | 19 | 100 |
| 3 | Et lactate (0.5 g) | MoO$_2$Cl$_2$(DMF)$_2$ 0.0291 g | TBHP (org) 1.5 ml | CH$_3$CN 10 g | 80 | 17 | 96 | 100 |
| 4 | Et lactate (0.5 g) | MoO$_2$Cl$_2$(benzthiozole) 0.0276 g | TBHP (org) 1.5 ml | CH$_3$CN 10 g | 80 | 15 | 70 | 100 |
| 5 | Et lactate (0.5 g) | MoO$_3$ 0.0276 g | TBHP (org) 1.5 ml | CH$_3$CN 10 g | 80 | 17 | 36 | 100 |
| 6 | Et lactate (0.5 g) | VO(acac)$_2$ 0.0215 g | TBHP (org) 1.5 ml | CH$_3$CN 10 g | 80 | 15 | 80 | 100 |
| 7 | Et lactate (0.5 g) | Copper acetate 0.0091 g | TBHP (org) 1.5 ml | CH$_3$CN 10 g | 80 | 11 | 46 | 100 |
| 8 | Methyl lactate (0.5 g) | MoO$_2$Cl$_2$(DMF)$_2$ 0.00330 | TBHP (org) 1.5 ml | CH$_3$CN 10 g | 80 | 14 | 43 | 100 |
| 9 | Et lactate (0.5 g) | MoO$_2$Cl$_2$(DMF)$_2$ 0.0291 g | TBHP (org) 1.5 ml | No solvent | RT | 36 | 3 | 100 |
| 10 | Et lactate (0.5 g) | MoO$_2$Cl$_2$(DMF)$_2$ 0.0291 g | TBHP (org) 1.5 ml | CH$_3$CN 10 g | 50 | 11 | 6 | 100 |
| 11 | Et lactate (0.5 g) | CoCl$_2$ 0.0199 g | TBHP (org) 1.5 ml | CH$_3$CN 10 g | 80 | 11 | 82 | 100 |
| 12 | Et lactate (0.5 g) | MoO$_2$Cl$_2$(DMF)$_2$ 0.0144 | TBHP (org) 1.5 ml | CH$_3$CN 10 g | 80 | 11 | 56 | 100 |
| 13 | Et lactate (0.5 g) | MoO$_2$Cl$_2$(DMF)$_2$ 0.0172 g | TBHP (org) 1.5 ml | CH$_3$CN 10 g | 80 | 11 | 11 | 100 |
| 14 | Et lactate (0.5 g) | MoO$_2$Cl$_2$(DMF) 0.072 | TBHP (org) 1.5 ml | CH$_3$CN 10 g | 80 | 11 | 72 | 100 |
| 15 | Et lactate (0.5 g) | MoO$_2$Cl$_2$(DMF)$_2$ 0.0291 | TBHP (org) 1.5 ml | CH$_3$CN 10 g | R.T | 38 | 5 | 100 |
| 16 | Et lactate (0.5 g) | FeCl$_3$ 0.0137 g | TBHP (org) 1.5 ml | CH$_3$CN 10 g | 80 | 9 | 63 | 100 |
| 17 | Et lactate (0.5 g) | MoO$_2$Cl$_2$(DMF)$_2$ 0.0291 g | TBHP (org) 1.5 ml | No solvent | 80 | 10 | 27 | 100 |
| 18 | Et lactate (0.5 g) | Silver nitrate 0.0143 g | TBHP (org) 1.5 ml | CH$_3$CN 10 g | 80 | 10 | 62 | 100 |
| 19 | Et lactate (0.5 g) | Palladium acetate 0.0189 g | TBHP (org) 1.5 ml | CH$_3$CN 10 g | 80 | 11 | 36 | 100 |

TABLE 1-continued

Catalytic activity data for lactate to pyruvate

| Example No. | Substrate | Catalyst, loading | Oxidant | Solvent | Temp ° C. | Time h | Conversion % | Sel. % |
|---|---|---|---|---|---|---|---|---|
| 20 | Et lactate (0.5 g) | Platinum(II)acetylacetone 0.0332 g | TBHP (org) 1.5 ml | CH$_3$CN 10 g | 80 | 9 | 56 | 100 |
| 21 | Et lactate (0.5 g) | Gold chloride 0.0256 g | TBHP (org) 1.5 ml | CH$_3$CN 10 g | 80 | 24 | 94 | 100 |
| 22 | Et lactate (0.5 g) | Nickel chloride 0.0109 g | TBHP (org) 1.5 ml | CH$_3$CN 10 g | 80 | 24 | 96 | 100 |
| 23 | Et lactate (0.5 g) | Ruthenium(III)acetylacetonate 0.0337 g | TBHP (org) 1.5 ml | CH$_3$CN 10 g | 80 | 10 | 50 | 100 |
| 24 | Et lactate (0.5 g) | Potassium dichromate 0.0248 g | TBHP (aq) 1.5 ml | CH$_3$CN 10 g | 80 | 10 | 68 | 100 |
| 25 | Et lactate (0.5 g) | Sodium tungstate 0.0279 g | TBHP (aq) 1.5 ml | CH$_3$CN 10 g | 80 | 10 | 12 | 100 |
| 26 | Et lactate (0.5 g) | Potassium titanium oxalate 0.0299 g | TBHP (aq) 1.5 ml | CH$_3$CN 10 g | 80 | 6 | 9.3 | 100 |
| 27 | Et lactate (0.5 g) | VO(acac)$_2$ 0.0215 g | MCPBA 1.4 g | CH$_3$CN 10 g | 80 | 24 | 50 | 100 |

Advantages of the Present Invention

Mild reaction conditions
Very high conversion up to 98%
Very high selectivity up to 100%
No polymerization observed

What is claimed is:

1. A one-step oxidative dehydrogenation process for the synthesis of an alkyl pyruvate from an alkyl lactate in the presence of a metal catalyst at a temperature ranging from 25-100° C. for a time period ranging from 5 to 40 hours in a peroxide selected from the group consisting of tert-butyl hydrogen peroxide and meta-chloroperbenzoic acid and optionally in a solvent to obtain the alkyl pyruvate,
wherein the metal catalyst comprises:
a metal selected from the group consisting of Co, Cr, Fe, Mo, W, Ti, Cu, Cr, Mn, Ag, Au, Ni, Pd, or Pt; and one or more species bound to the metal selected from the group consisting of oxo, a halide, DMSO, DMF, bipyridine, benzthiazole, acetate, nitrate, and acetylacetonate.

2. The process as claimed in claim 1, wherein said alkyl lactates are selected from the group consisting of methyl lactate, ethyl lactate, propyl lactate and butyl lactate.

3. The process as claimed in claim 1, wherein said solvent is selected from the group consisting of water, acetonitrile, methanol, ethanol and toluene.

4. The process as claimed in claim 1, wherein said process is carried out without solvent.

5. The process as claimed in claim 1, wherein said process has a selectivity towards pyruvate formation of greater than 90%.

6. The process as claimed in claim 1, wherein said process provides greater than 90% conversion of alkyl lactates.

* * * * *